(12) United States Patent
Kath et al.

(10) Patent No.: US 7,735,366 B2
(45) Date of Patent: Jun. 15, 2010

(54) METHOD AND APPARATUS FOR MEASURING THE VOLUME OF AN ANIMAL PAW

(75) Inventors: Gary S. Kath, Scotch Plains, NJ (US);
Michael K. Wismer, Rahway, NJ (US);
Paul R. Augustine, Carteret, NJ (US);
Cordelia G. Rasa, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 218 days.

(21) Appl. No.: 10/536,120

(22) PCT Filed: May 6, 2006

(86) PCT No.: PCT/US2006/017368

§ 371 (c)(1),
(2), (4) Date: Oct. 15, 2007

(87) PCT Pub. No.: WO2006/124328

PCT Pub. Date: Nov. 23, 2006

(65) Prior Publication Data

US 2009/0282913 A1    Nov. 19, 2009

Related U.S. Application Data

(60) Provisional application No. 60/679,941, filed on May 11, 2005.

(51) Int. Cl.
*G01N 9/10* (2006.01)
*G01G 5/00* (2006.01)

(52) U.S. Cl. .......................................... 73/437; 33/1 V
(58) Field of Classification Search ................... 73/437, 73/149, 435, 426; 33/1 V
See application file for complete search history.

(56) References Cited

U.S. PATENT DOCUMENTS

| | | |
|---|---|---|
| 2,650,494 A | 9/1953 | Linhorst |
| 3,747,416 A | 7/1973 | Wommack |
| 4,372,405 A | 2/1983 | Stuart |

*Primary Examiner*—Christopher W Fulton
(74) *Attorney, Agent, or Firm*—Maria V. Marucci; Valerie J. Camara

(57) ABSTRACT

Disclosed is an improved method for measuring the volume of an animal paw, suitable for use in a rat paw edema assay. Also disclosed is a novel apparatus for measuring the volume of liquid displaced by the insertion of an object into a liquid filled cup (1) which is on a cup holder basin (3), the liquid filled cup and cup holder basin being inside a rectangular support assembly (5), the measurement obtained by determining the buoyant force produced as a result of the displacement of the liquid by the animal paw.

11 Claims, 4 Drawing Sheets

METHOD AND APPARATUS FOR MEASURING THE VOLUME OF AN ANIMAL PAW

CROSS REFERENCE TO RELATED APPLICATIONS

This application is a U.S. National Phase application under 35 U.S.C. §371 of PCT Application No. PCT/US2006/017368, filed, May 5, 2006, which claims priority under 35 U.S.C. §119(e) from U.S. Provisional Application Ser. No. 60/679,941, filed, May 11, 2005.

BACKGROUND OF THE INVENTION

This invention relates to a method and apparatus for measuring the volume of an object by liquid displacement. In particular, this invention relates to the measurement of the increase in volume of the paw of an animal, the increase due to the inflammation of the paw. An instrument of this type has been described as a plethysmometer.

The present invention may be used in the so called, rat paw edema assay, the rat adjuvant arthritis assay and functionally related models. An adjuvant arthritis model is illustrated below. The, so called, rat paw edema assay, is a classic assay used to assess the ability of a putative anti-inflammatory agent to prevent the edema that would otherwise have been produced by the injection of a pro-inflammatory agent. See Winter et. al., *Proc. Soc. Exp. Biol. Med.*, 111, 544 (1962). WO 95/18799, published Jul. 13, 1995 describes one such assay as follows:

"Male Sprague-Dawley rats (150-200 g) were fasted overnight and were given to either vehicle (5% Tween 80 or 1% Methocel) or a test compound at 9-10 a.m. One hr later, a line was drawn using a permanent marker at the level above the ankle in one hind paw to define the area of the paw to be monitored. The paw volume ($V_{Oh}$) was measured using a plethysmometer (Ugo-Basile, Italy) based on the principle of water displacement. The animals were then injected subplantarly with 50 µl of a 1% carrageenan solution in saline (FMC Corp., Maine) into the paw using an insulin syringe with a 25-gauge needle (i.e. 500 g of carrageenan per paw). Three hr later, the increases in paw volume ($V_{3h}$-$V_{Oh}$) were measured."

Illustrative of plethysmometers sold for purposes of conducting such assays are those sold by Buxco, Electronics; Muromachi Kikai Co., Ltd.; and Ugo Basile.

Historically applicants used an in-house system that was developed in the 1970's and in the 1990's purchased a commercial unit from Buxco®. Both of these methods for determination of paw volume changes are based on fluid pressure measurement. They are more difficult to use, prone to sensor drift, and susceptible to errors caused by trapped air bubbles or improper priming.

This application presents a new method for paw volume determination, and compares the accuracy of this system to a representative reference system.

SUMMARY OF THE INVENTION

Disclosed is an improved method for measuring the volume of an animal paw, suitable for use in a rat paw edema assay. Also disclosed is a novel apparatus for measuring the volume of liquid displaced by the insertion of an object into a liquid filled container, the measurement obtained by determining the buoyant force produced as a result of the displacement of the liquid by the object.

DETAILED DESCRIPTION OF THE INVENTION

In one aspect, the invention encompasses an apparatus (or unit) useful for measuring with a laboratory balance the volume of an object, such as a paw, said apparatus comprising:

(a) a mercury cup;

(b) a cup holder basin; and (c) a support assembly;

said mercury cup being an open container suitable for holding liquid mercury and having inside horizontal dimensions larger than the outside horizontal dimensions of said object;

said cup holder basin having a top and a bottom;

said top having a continuous sidewall and a continuous interior wall forming a spill basin for retaining said liquid mercury there between, said interior wall forming an interior space for holding said mercury cup;

said bottom being suitable for resting said cup holder basin on the weighing mechanism of said laboratory balance;

said support assembly comprising:

(a') a top plate, said top plate comprising an access port through which said mercury cup can be accessed and retrieved;

(b') at least two side supports, each of said side supports attached to said top plate; and (c') at least two support brackets, each of said support plates attached to one of said side supports and attached to a fixed member of said laboratory balance.

Optionally the top plate further comprises a depression, said depression surrounding said access port, said depression having a pass through port for allowing liquid mercury to be transported from said depression to said cup holder basin.

Optionally, the top plate further comprises a paw guide removably attached to said top plate, said paw guide having an opening larger than the outside horizontal dimensions of said object, such as a paw, and smaller than the horizontal inside dimensions of said mercury cup.

Figure 1:
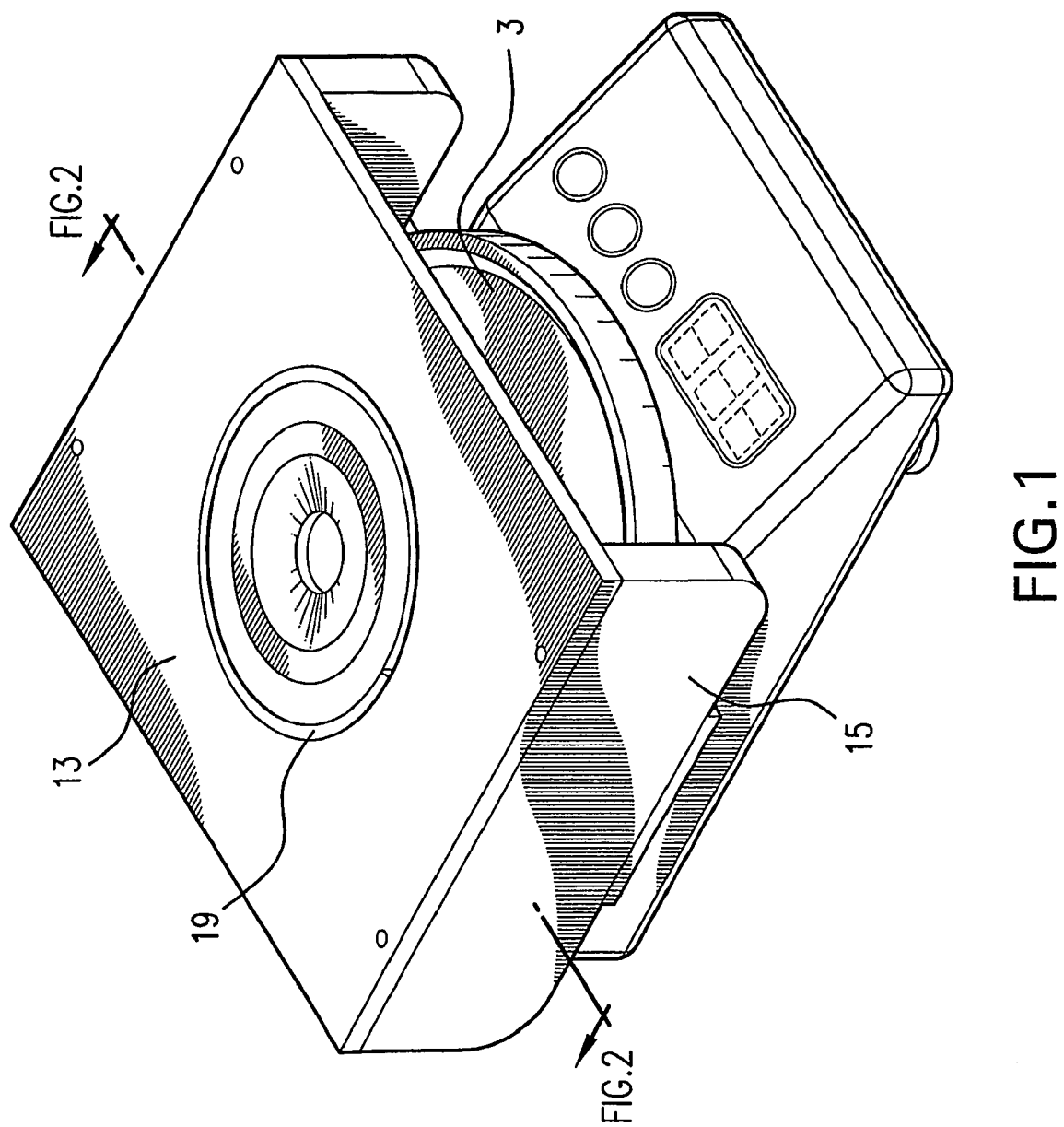
FIG. 1 discloses a perspective view of the preferred embodiment on a laboratory scale.
Figure 2:
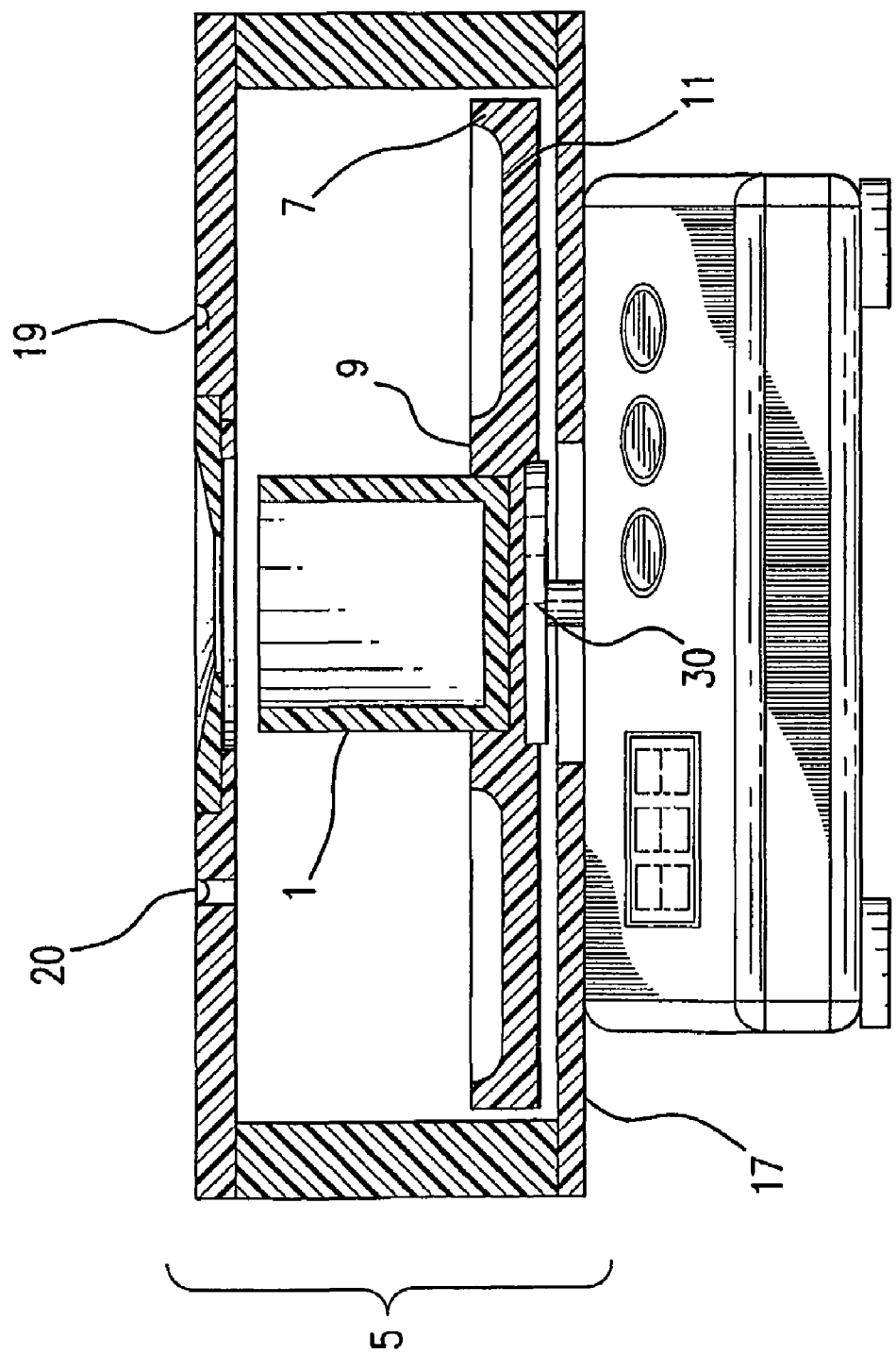
FIG. 2 discloses a cut away view of the preferred embodiment on a laboratory scale.
Figure 3:
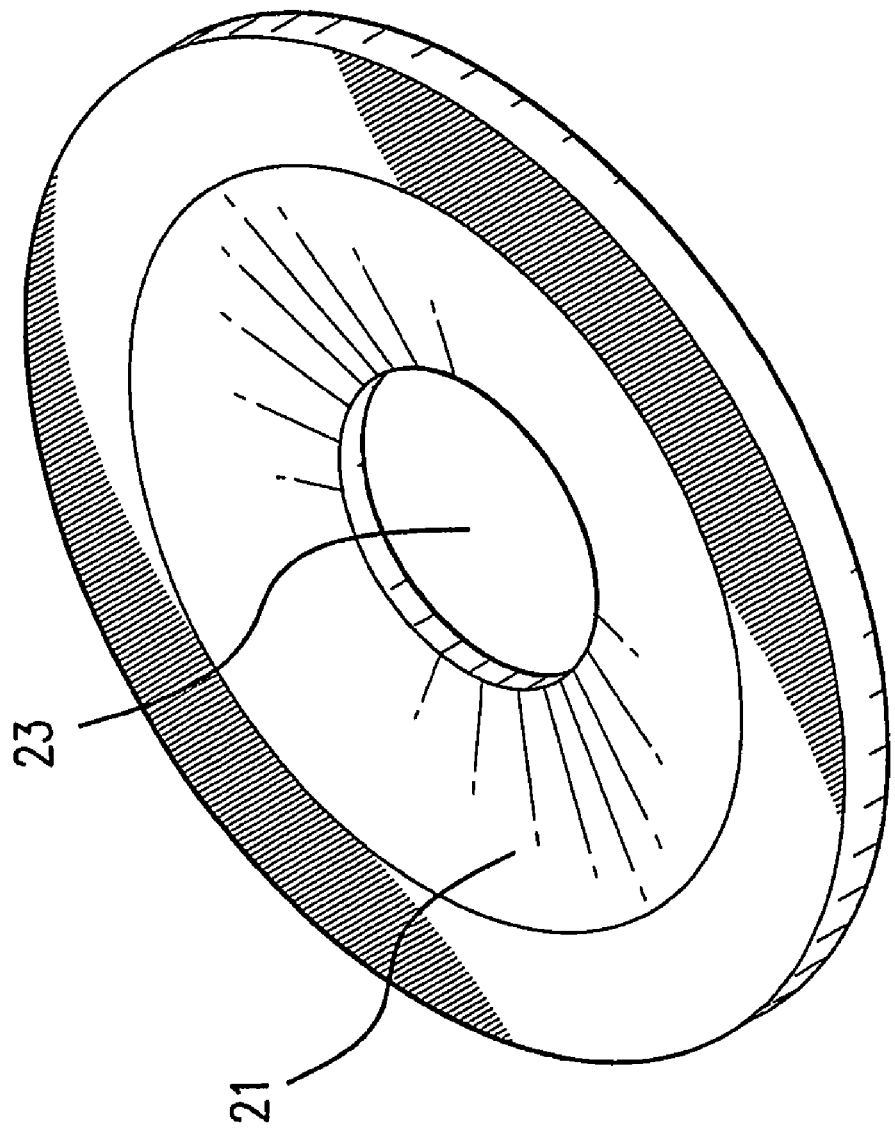
FIG. 3 discloses a preferred embodiment of a paw guide.

A preferred embodiment is shown in FIG. 1, FIG. 2 and FIG. 3. This preferred embodiment encompasses an apparatus useful for measuring on a laboratory balance the volume of a paw, said apparatus comprising:

(a) a mercury cup [1];

(b) a cup holder basin [3]; and (c) a rectangular support assembly [5];

said mercury cup [1] being an open cylindrical container suitable for holding liquid mercury and having inside horizontal dimensions larger than the outside horizontal dimensions of said paw;

said cup holder basin [3] being round and having a top and a bottom;

said top having a continuous sidewall [7] and an interior wall [9] forming a spill basin [11] for retaining said liquid mercury there between, said interior wall forming an interior space for holding said mercury cup [1];

said bottom being suitable for resting said cup holder basin on the weighing mechanism [30] of said laboratory balance; and said rectangular support assembly [5] comprising:

(a') a top plate [13], said top plate [13] comprising an access port through which said mercury cup can be accessed and retrieved;

(b') at least two side supports [15], said side supports [15] removably attached to said top plate [13]; and (c') at least two support brackets [17], each of said support brackets [17] removably attached to one of said side supports [15] and removably attached to a fixed member said laboratory balance.

Optionally the top plate [13] further comprises a depression [19], said depression [19] surrounding said access port, said depression [19] having a pass through port [20] for allowing liquid mercury to be transported from said depression to said cup holder basin [3].

Optionally, the top plate [13] further comprises a paw guide [21] which can be removably attached to said top plate [13], said paw guide [21] having an opening [23] larger than the outside horizontal dimensions of said paw and smaller than the horizontal inside dimensions of said mercury chamber [1].

As will be appreciated by one of skill in the art, the support assembly is constructed in a manner that will allow the operator to rest his or her hands of the top plate without affecting the measurement of the object. Thus, the support plates are attached to a stable portion of the balance, not connected to the weighing mechanism. For purposes of this specification a stable portion of the balance, not connected to the weighing mechanism is called a "a fixed member of said laboratory balance"

In one aspect, the mercury cup of the preferred embodiment may be an open cylinder having an inside horizontal diameter of 4 to 6, preferably 4.4 to 5.75 cm and may hold from approximately 50 to 175 ml of mercury.

In one aspect the cup holder basin of the preferred embodiment may be 20 to 26, preferably 20.25 to 25.5 cm in outside diameter. The continuous sidewall and continuous inside wall together form a reservoir sufficient to retaining at least 10% of the volume of the mercury chamber.

In one aspect the top plate is made of a clear material, such as glass or plastic so that the mercury chamber is easily visible from above. Preferably, the top plate is attached to the side supports by screws, pins or glue. Preferably, the side supports are attached to the support brackets by screws, pins or glue. Preferably the support bracket is attached to the scale by screws or bolts.

In one aspect said depression in said top plate is slanted toward said pass through port, to enhance the movement of liquid mercury from said depression into said cup holder basin.

In another embodiment, the invention is directed to the use of the apparatus described above for measuring the buoyant force produced by displacing a volume of mercury with a paw.

In another embodiment, the invention is directed to a method of measuring the volume of a paw comprising measuring the buoyant force produced by displacing a volume of liquid. Preferably, the liquid is mercury.

The present system works by measuring the buoyant force produced by displacing mercury. In general, the prior art systems measure the change in fluid pressure due to the change in the height of the mercury in the measuring vessel.

Prior units used for paw volume determination which rely on measuring, indirectly, the volume of liquid displaced by submerging the paw into a container filled with mercury. In particular, the prior unit measures the change in fluid pressure as a result of the change in height of the mercury in the measuring vessel. In contrast, the apparatus of the present invention works by measuring the buoyant force produced by displacing the mercury. In the example below, studies were run in the rat adjuvant model to compare the results obtained using the present invention and a prior unit.

An Example of the Present Invention

The present apparatus (FIG. 1, FIG. 2 and FIG. 3) consists of a cylindrical container, constructed of acrylic, which sits on the balance pan of a force-restoration balance. This container is filled with liquid mercury. The balance pan is fabricated with a lip to contain any mercury that may spill out of the container during measurement. The inside diameter (5.080 cm) and depth (5.715 cm) of the container are such that a paw may be submerged in the mercury without touching the bottom or the sides of the container. Surrounding the sides and the top of the balance and the container is a draft shield that may also be used as a hand-rest when taking measurements. The balance and a set of foot pedals are connected to a computer, which runs a custom Visual Basic.NET® program to automate the collection of data.

To take a measurement, the balance is zeroed. The user then holds the leg to be measured so that the paw is submerged in the mercury, up to a reference line on the leg of the animal. Care is taken not to allow the paw to touch the sides or the bottom of the container, as any contact with the balance pan or the container holding the mercury will cause measurement errors. The balance reading is displayed in real-time on the computer screen. When the balance reading has settled to a stable value, the user depresses a footswitch to record the displayed value.

The force recorded by the balance is the force exerted by the user to cancel the buoyant force that results when the volume of mercury is displaced by the paw of the animal. The displaced volume is then equal to the buoyant force divided by the density of the mercury ($\Delta V = F_b/\rho_1$). The GF-4100 balance used has a capacity of 4100 g and a resolution of 10 mg (A&D Company, Ltd., Tokyo, Japan). Using mercury as the working fluid (liquid density ($\rho_1$)=13.54587 g/mL at 20° C.), the resolution of the instrument is 0.010 g/13.54587 g/mL=0.74 uL (6).

The apparatus is calibrated before a study using 2 Teflon spheres of known diameter. Each sphere is attached to the end of a stainless steel needle. The sphere is submerged just under the surface of the mercury, and the balance reading is taken.

Old System. Briefly, an old unit, used for reference purposes, also consists of a cylindrical acrylic chamber filled with liquid mercury. This chamber sits above a lower chamber which is coupled to a pressure transducer. The change in volume is equal to the change in pressure times the cross-sectional area divided by the liquid density ($\Delta V = (\Delta p A)/\rho_1$). The resolution of this instrument is 10 uL. This instrument is calibrated at zero and with a Teflon calibration cylinder of known volume.

Animals. Rats were housed in a conventional facility, had access to standard rodent laboratory diet (Harland Teklad Laboratory Rodent Diet 7012) and reverse-osmosis water ad libitum and were maintained on a 12 h light/dark cycle. Sentinel animals were evaluated quarterly as part of a health surveillance program and were determined to be specific pathogen free by Charles River Laboratory Assesment Plus profile (Wilimington, Mass.), endo- and ectoparasite examinations and gross necropsy.

Adjuvant studies were run with 10 animals per treatment in which rats were divided into 3 boxes of 4, 3 and 3 rats each per box.

Adjuvant preparation. Adjuvant was made by grinding Mycobacterium tuberculosis and suspending it in light mineral oil (5 mg/20 ml). The suspension was prepared 30 minutes prior to injection and continuously spun with a stir bar until injected.

Adjuvant arthritis. Female, seven week-old, Lewis rats (Charles River, Raleigh, N.C.) were weighed, ear marked and assigned to groups. A line was tattooed onto each ankle just above the lateral malleolus on day −3 to act as a stop-line during paw volume acquisition. Rats were anesthetized at a rate of 1 ml/10 g with ketamine (100 mg/ml)/xylazine (100 mg/ml) (9:1) and injected in the left plantar surface (primary paw) of the rats between the $3^{rd}$ and $4^{th}$ digits with 0.1 ml of adjuvant. Adjuvant-injected groups consisted of 10 rats per treatment, healthy, control rats were five per housing-condition.

Rats were on study for 21 days and paw volumes were measured as per Table 1.

TABLE 1

Treatments and data time-points.

| Treatment | Number of rats per box | Days of paw volume measurement |
|---|---|---|
| Control | 3, 2 | 0, 14, 21 |
| Control | 5 | 0, 14, 21 |
| Adjuvant Arthritis | 4, 3, 3 | 0, 14, 21 |
| Adjuvant Arthritis | 4, 3, 3 | 0, 1, 3, 4, 7, 9, 11, 14, 16, 18, 21 |
| Adjuvant Arthritis | 4, 3, 3 | 0, 14, 21 |
| Adjuvant Arthritis | 5, 5 | 0, 14, 21 |
| Adjuvant Arthritis | 4, 3, 3 | 0, 1, 3, 4, 7, 9, 11, 14, 16, 18, 21 |
| Adjuvant Arthritis | 5, 5 | 0, 1, 3, 4, 7, 9, 11, 14, 16, 18, 21 |

A—Ancare
T—Tecniplast
i—Infrequent handling
f—frequent handling
-#-#—number of animal per each box Volume readings were taken using both the old and new plethysmograph apparatus. Each measurement was acquired by dipping the hind paws of each rat into the mercury up to a tattoo on the ankle. Each housing paradigm was further tested under frequent and infrequent handling. The frequently handled rats were measured multiple times to confirm normal progression of the disease. Infrequently-handled rats were measured on days that would correspond with data points normally collected during drug evaluation studies.

Statistical Analysis Statistics were run on CMG StatServer (version 2.93) using two-way anova and t-test analysis with the confidence interval set to the $95^{th}$ percentile.

Results

Figure 4:
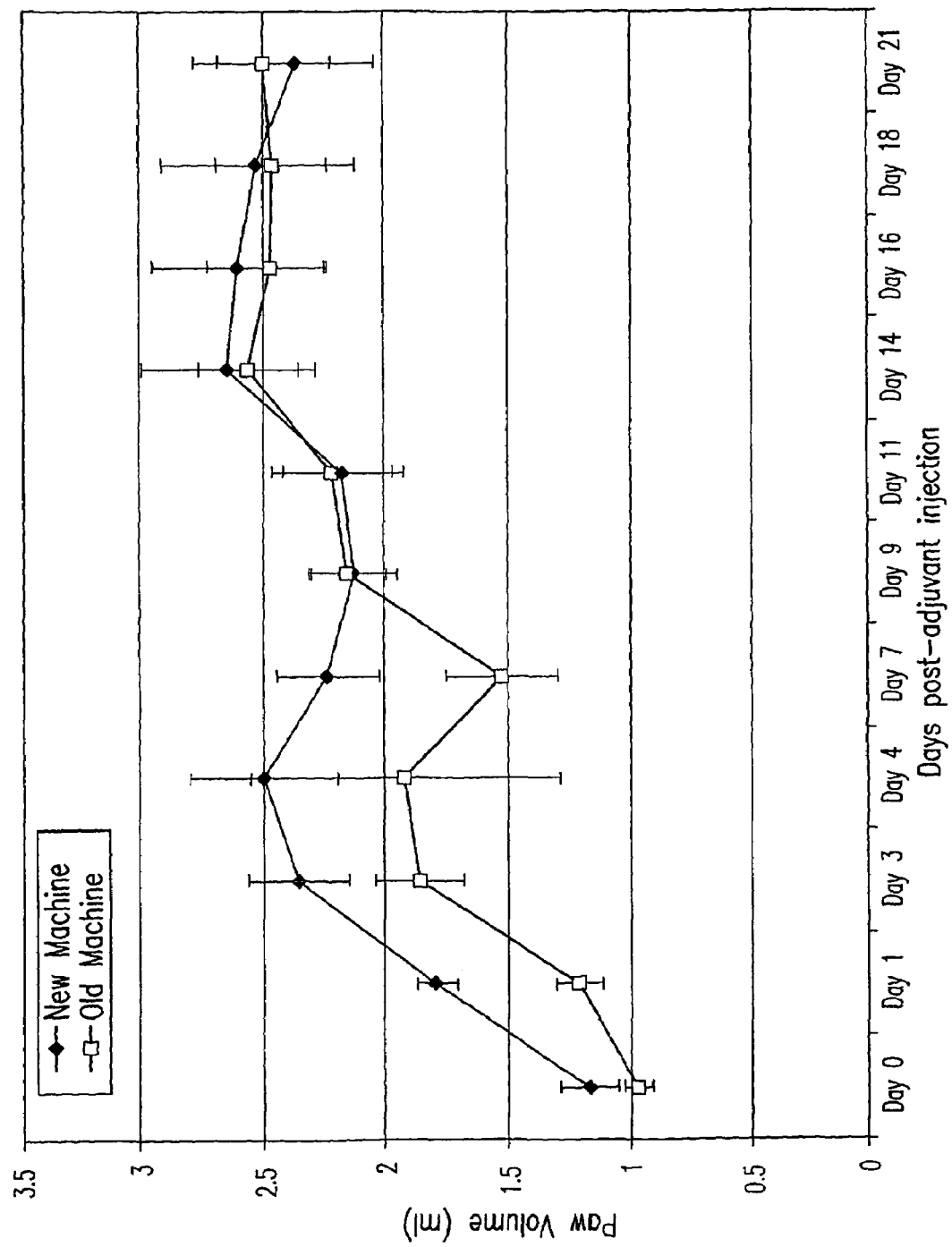
FIG. 4 discloses a comparison of rat paw volume as measured with the new apparatus and a reference apparatus. As shown, the discrepancy in volumes measured by each unit in the first week was eliminated with the identification and removal of an air bubble in the mercury column of the old unit.

The data collected from the old apparatus were inaccurate for several days until an air bubble in the mercury was identified and removed. Once the correction was made the data were almost identical and not statistically different from the new machine (FIG. 4).

Discussion

Several difficulties encountered with the older apparatus are eliminated with the new plethysmograph. The new apparatus has a larger opening diameter which eliminates the risk of damaging swollen paws by attempting to force them into a narrow opening. The new apparatus also allows adjustment of the dipping area by placing disks with openings of different diameters over the mercury. The disks also ensure the paws are dipped in the center of the mercury vessel.

The foot pedals were developed to simplify data collection. Each tap of the foot pedal corresponds to a data point. The option to re-take a measurement is on a separate pedal. This reduces any errors in data collection by accidental foot depressions or sequences of foot pedal depressions while collecting data. In order to re-take a measurement you have to make a deliberate attempt to reach the pedal.

A benefit of having the new apparatus created in-house was the development of custom software to accompany it. The program was written for us with our specific needs in mind which significantly reduced the time we spent collecting and analyzing data. Our data is collected electronically and placed directly into the format we use for statistical analysis.

The software also forces the user to calibrate the instrument each time it is used. The system is calibrated by the measuring two known volumes. This calibration corrects for changes in the density of the measuring fluid due temperature or contamination. The old apparatus required calibration checks during data collection. Since drift is not a concern with the new apparatus, calibration only occurs once at the beginning of an experiment. The commercial Buxco unit also only recommended one calibration, but additional calibrations had to be incorporated during studies due to drift over time.

Additional precautions were needed when taking measurements with the older apparatus. The measuring liquid needed to be as clean as possible, and at a stable temperature. The pressure transducer had to warm-up for at least one hour prior to taking any measurements.

The comparison of the old and new apparatus not only illuminated the ease of use of the new machine, but also highlighted one of the problems with the old apparatus. The discrepancies in volume measurement as seen on days 1 through 7 were eliminated once we located an air bubble and removed it. The mercury had to be removed, strained and carefully reintroduced to the old apparatus.

As a working fluid, mercury provides several advantages over water. First, it does not wet to many surfaces. This reduces working fluid loss as the paws are removed. Second, it has a much higher density ($\rho_1 = 13.54587$ g/mL at 20° C.) than water ($\rho_1 = 0.998204$ g/mL at 20° C.)(6). The high density causes most contaminants to float to the top of the container, where they can easily be removed. When used with either machine, the mercury provides a larger signal amplitude, due to its higher density. However, water may also be substituted for mercury, due to financial or environmental concerns. In-house tests were run to assess the safety of mercury during our studies, and under the conditions we operate in there were no concerns.

Both of the units used for paw volume determination rely on measuring, indirectly, the volume of liquid displaced by submerging the paw into a container filled with mercury. The new unit works by measuring the buoyant force produced by displacing the mercury. The old unit measures the change in fluid pressure as a result of the change in height of the mercury in the measuring vessel.

The older unit measures the volume of the paw by recording the change of pressure at a fixed point within the liquid. The change in fluid height is equal to the change in pressure divided by the liquid density ($\Delta h = \Delta p / \rho_1$). For a container with smooth, parallel vertical surfaces, the change in volume is equal to the change in fluid height times the cross-sectional area ($\Delta V = \Delta h * A$). The change in fluid height is determined by measuring the change in fluid pressure at the bottom of the container. Note that decreasing the cross-sectional area of the container increases the change in fluid height, resulting in a larger pressure change. This means that the diameter of the measuring chamber should be no larger than needed to admit the largest swollen paw.

The new unit measures the volume of the paw by measuring the force that the operator exerts to keep the rat's paw submerged. The volume of the submerged paw is equal to the buoyant force divided by the liquid density ($\Delta V = F_b / \rho_1$). To measure this force, the container is placed on a force-restoration balance. A simple two-point calibration is used to compensate for changes in mercury density due to temperature or contamination. The force restoration balance provides the large dynamic range needed to measure the small buoyant force, which is superimposed on the larger static force due to the weight of the container and its liquid. Cleaning and filling of the container can be performed easily, as a simple cylindrical container may be used. In addition, the opening of the container may be quite large, as the parameter to be measured is independent of the cross-sectional area of the container.

In summary, the new plethysmograph unit affords us an efficient and reliable tool for generating volumetric data. The new system can easily be replicated by other investigators for rapid and reliable data generation.

What is claimed is:

1. An apparatus useful for measuring on a laboratory balance the volume of an object, said apparatus comprising:
   (a) a mercury cup;
   (b) a cup holder basin; and
   (c) a support assembly;
   said mercury cup being an open container suitable for holding liquid mercury and having inside horizontal dimensions larger than the outside horizontal dimensions of said object;
   said cup holder basin having a top and a bottom;
      said top having a continuous sidewall and a continuous interior wall forming a spill basin for retaining said liquid mercury there between, said interior wall forming an interior space for holding said mercury cup;
      said bottom being suitable for resting said cup holder basin on the weighing mechanism of said laboratory balance;
   said support assembly comprising:
   (a') a top plate, said top plate comprising an access port through which said mercury cup can be accessed and retrieved;
   (b') at least two side supports, each of said side supports attached to said top plate; and
   (c') at least two support brackets, each of said support brackets attached to one of said side supports and removably attached to a fixed member of said laboratory balance.

2. An apparatus according to claim 1 wherein said top plate further comprises a depression, said depression surrounding said access port, said depression having a pass through port for allowing liquid mercury to be transported from said depression to said cup holder basin.

3. An apparatus according to claim 1 wherein said top plate further comprises an object guide which can be removably attached to said top plate, said object guide having an opening larger than the outside horizontal dimensions of said object and smaller than the horizontal inside dimensions of said mercury chamber.

4. An apparatus useful for measuring on a laboratory balance the volume of a paw, said apparatus comprising:
   (a) a mercury cup;
   (b) a cup holder basin; and
   (c) a rectangular support assembly;
   said mercury cup being an open cylindrical container suitable for holding liquid mercury and having inside horizontal dimensions larger than the outside horizontal dimensions of said paw;
   said cup holder basin being round and having a top and a bottom;
      said top having a continuous sidewall and an interior wall forming a spill basin for retaining said liquid mercury there between, said interior wall forming an interior space for holding said mercury cup;
      said bottom being suitable for resting said cup holder basin on the weighing mechanism of said laboratory balance; and
   said rectangular support assembly comprising:
   (a') a top plate, said top plate comprising an access port through which said mercury cup can be accessed and retrieved;
   (b') at least two side supports, said side supports removably attached to said top plate; and
   (c') at least two support brackets, each of said support brackets removably attached to one of said side supports and removably attached to a fixed member of said laboratory balance.

5. An apparatus according to claim 4 wherein said the top plate further comprises a depression, said depression surrounding said access port, said depression having a pass through port for allowing liquid mercury to be transported from said depression to said cup holder basin.

6. An apparatus according to claim 4 wherein said top plate further comprises a paw guide which can be removably attached to said top plate, said paw guide having an opening larger than the outside horizontal dimensions of said paw and smaller than the horizontal inside dimensions of said mercury cup.

7. An apparatus according to claim 4 wherein said mercury cup is an open cylinder having an inside horizontal diameter of 4.0 to 6.0 cm and holds from approximately 50 to 175 ml of mercury.

8. An apparatus according to claim 4 wherein said cup holder basin is 20 to 26 cm outside diameter and said continuous sidewall and continuous inside wall together form a spill basin sufficient to retain at least 10% of the volume of the mercury cup.

9. An apparatus according to claim 4 wherein said top plate is made of a clear material.

10. An apparatus according to claim 4 wherein said depression in said top plate is slanted toward said pass through port, to enhance the movement of liquid mercury from said depression into said cup holder basin.

11. Use of the apparatus of claim 4 for measuring the buoyant force produced by displacing a volume of mercury with a paw.

* * * * *